United States Patent [19]

Hinshaw et al.

[11] 4,218,368

[45] Aug. 19, 1980

[54] AROMATIC NITRO COMPOUNDS CONTAINING DIFFUSIBLE GROUPS CLEAVABLE BY INTRAMOLECULAR NUCLEOPHILIC DISPLACEMENT

[75] Inventors: Jerald C. Hinshaw, Penfield; Richard P. Henzel, Webster, both of N.Y.

[73] Assignee: Eastman Kodak Company, Rochester, N.Y.

[21] Appl. No.: 928,050

[22] Filed: Jul. 26, 1978

Related U.S. Application Data

[62] Division of Ser. No. 775,219, Mar. 7, 1977, Pat. No. 4,139,389.

[51] Int. Cl.$^2$ .................. C07C 107/00; C07C 107/04; C09B 43/16; C09B 43/18
[52] U.S. Cl. .................. 260/156; 252/390; 260/199; 260/207; 260/207.1; 260/154; 260/544 S; 260/574; 424/226; 548/241; 548/251; 546/226; 536/7; 544/368; 562/429; 562/432; 562/438; 568/766; 430/183; 430/202; 430/218; 430/225; 430/382; 430/541; 430/562
[58] Field of Search ............ 260/199, 156, 207, 207.1, 260/154

[56] References Cited

U.S. PATENT DOCUMENTS

| | | | |
|---|---|---|---|
| 2,681,364 | 6/1954 | Long et al. | 260/558 |
| 2,846,307 | 8/1958 | Woolley | 96/55 |
| 2,937,204 | 5/1960 | Harris et al. | 260/558 |
| 3,185,567 | 5/1965 | Rogers | 96/3 |
| 3,443,939 | 5/1969 | Bloom et al. | 96/3 |
| 3,443,940 | 5/1969 | Bloom et al. | 96/3 |
| 3,515,790 | 6/1970 | Burdeaka et al. | 424/309 |
| 3,516,982 | 6/1970 | Dimroth et al. | 260/207 X |
| 3,535,306 | 10/1970 | Altermatt et al. | 260/207 X |
| 3,658,885 | 4/1972 | Lange et al. | 260/207.1 X |
| 3,663,531 | 5/1972 | Liechti | 260/207 X |
| 3,728,113 | 4/1973 | Becker et al. | 96/3 |
| 3,741,954 | 6/1973 | Altermatt | 260/207 X |
| 3,751,406 | 8/1973 | Bloom | 260/199 X |
| 3,865,805 | 2/1975 | Altermatt | 260/207 X |
| 3,877,941 | 4/1975 | Lohmann | 96/48 R |
| 3,932,380 | 1/1976 | Krutak et al. | 260/149 X |
| 3,980,479 | 9/1976 | Fields et al. | 96/29 D |
| 4,108,850 | 8/1978 | Fields et al. | 260/199 X |
| 4,139,379 | 2/1979 | Chasman et al. | 96/3 |

OTHER PUBLICATIONS

Cox et al., J. C. S. Perkin II, 1975, pp. 1512–1515.
Panetta, *The Journal of Organic Chemistry*, 34, 1969, pp. 2773–2775.
Okano et al., *Journal of the Pharmaceutical Society of Japan*, vol. 89, No. 1, 1969, pp. 67–73.
Chemical Abstracts, vol. 73, 1970, No. 87902z, vol. 75, 1971, No. 76682t, vol. 74, 1971, No. 31778s.
Fearon et al., *The Biochemical Journal*, vol. 37, 1943, pp. 326–329.
Williams, JACS, 74, 1952, pp. 3069–3074.
Entwistle et al., J. C. S. Perkin I., 1975, pp. 1300–1301.
Johnstone et al., J. C. S. Perkin I., 1975, pp. 1424–1427.

*Primary Examiner*—Floyd D. Higel
*Attorney, Agent, or Firm*—Gerald E. Battist

[57] ABSTRACT

Aromatic nitro compounds are disclosed where the aromatic ring contains electron-withdrawing groups and said aromatic nitro compound is capable of undergoing intramolecular nucleophilic displacement after reduction of the nitro group. The compounds are especially useful in photographic elements where an image dye-providing material or a photographic reagent are released upon cleavage from the compound.

12 Claims, No Drawings

AROMATIC NITRO COMPOUNDS CONTAINING DIFFUSIBLE GROUPS CLEAVABLE BY INTRAMOLECULAR NUCLEOPHILIC DISPLACEMENT

This is a division of Ser. No. 775,219 filed Mar. 7, 1977, now U.S. Pat. No. 4,139,389 issued Feb. 13, 1979.

This invention relates to new compounds, new photographic elements and new processes for forming image records in photographic elements. The compounds of this invention that can be used in photographic elements and processes are dye-providing materials and photographic reagents that contain a cleavable substituent thereon. Generally, the cleavable moieties of the compounds of this invention require acceptance of at least one electron with subsequent intramolecular nucleophilic displacement to cleave or displace the moiety from its original substituent position. The cleavable substituents are useful in providing removable ballast groups, removable inactivating groups, removable substituents which shift the resonance of the molecule, and the like.

It is known in the art that certain blocking groups can be used on compounds temporarily to immobilize or inactivate the compound in a photographic element. Heavy counter ions, such as barium salts, have been used to immobilize dyes, as disclosed by Yutzy, U.S. Pat. No. 2,756,142 issued July 24, 1956. Removable ballast groups on dyes or photographic reagents are also described by Whitmore, Canadian Pat. No. 602,607 issued Aug. 2, 1960, and U.S. Pat. Nos. 3,227,552, 3,628,952, 3,728,113, 3,725,062 and the like. Compounds that undergo intramolecular ring closure upon oxidation to split off a dye are disclosed in U.S. Pat. Nos. 3,443,939, 3,443,940, 3,443,941 and 3,751,406. Compounds that are initially immobile and undergo a redox reaction followed by alkali cleavage to split off a dye are disclosed by Fleckenstein et al, Published U.S. Ser. No. B351,673 filed Apr. 16, 1973.

It is also known in the prior art that intramolecular nucleophilic displacement compounds containing an hydroxylamino nucleophile can be used in photographic elements to release a diffusible image dye-providing material or a photographic reagent, as shown by Hinshaw and Condit, U.S. Ser. No. 534,966 filed Dec. 20, 1974, and Fields et al, U.S. Pat. No. 3,980,479 issued Sept. 14, 1976.

We have now discovered improved compounds that will undergo intramolecular nucleophilic displacement and that offer certain advantages when used in products such as photographic elements and the like in controlling the release of a dye-providing moiety or a photographic reagent. Generally, the compounds of this invention are aromatic nitro compounds which, upon accepting electrons (reduction), undergo intramolecular nucleophilic displacement to release an image dye-providing moiety or a photographic reagent.

Aromatic nitro compounds have been known in the art for several years, for example, as disclosed in U.S. Pat. Nos. 2,938,204 issued May 17, 1960, and 2,681,364 issued June 15, 1954; *Biochemical J.*, 37, 326 (1943); *Yakugaku Zasshi*, 89, 67 (1969); *J. Chem. Soc.*, 2393 and 2398 (1971); etc. Aromatic nitro compounds have also been suggested for use in photographic elements, for example, as disclosed in U.S. Pat. No. 3,877,941, where an aromatic nitro compound is used as an amine progenitor.

However, we have now found that certain aromatic nitro compounds in accordance with this invention provide highly advantageous results in the release of image dye-providing materials or the release of photographic reagents. Generally, the useful compounds are based on an aromatic nitro compound that contains at least one other group, which is an electron-withdrawing group, in the aromatic ring or as a substituent of the aromatic ring. Where the compounds are designed for photographic uses, at least one substituent on the ring comprises an image dye-providing moiety or a photographic reagent separated from the ring by an electrophilic cleavage group that contains an electrophilic center and a leaving group that is capable of being displaced by intramolecular nucleophilic displacement upon the reduction of said nitro group.

In the broad concepts of this invention, we have discovered cleavable moieties which can be put on any molecule through a linkage atom which is an oxygen atom, a sulfur atom, a nitrogen atom or a selenium atom. The cleavable moieties can be used to control the time and rate of release of the compound, and upon reduction undergo intramolecular nucleophilic displacement of the linkage atom, along with the moiety linked through the atom. While this cleavage mechanism is particularly useful for photographic reagents and image dye-providing moieties, it is also useful for releasing pharmaceuticals, corrosion inhibitors and the like.

The compounds of the present invention offer several advantages; for example, the reduction prior to intramolecular displacement can be accomplished with organic reducing agents under mild conditions such as encountered in many photographic processes. In contrast, nitro compounds are reduced according to several prior-art disclosures by hydrogenation in the presence of a noble-metal catalyst.

In certain preferred embodiments, the compounds of this invention have the formula:

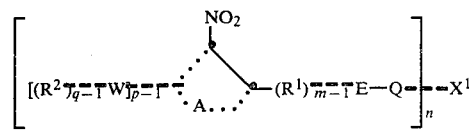

where A represents a group containing the atoms necessary to form a 5- to 6-membered aromatic ring with the remainder of said formula, including polycyclic aromatic ring structures, and wherein the aromatic rings can be carbocyclic rings or heterocyclic rings such as groups containing aromatic 'onium groups in the ring, and A preferably represents the groups necessary to form a carbocyclic ring system such as a benzene ring, a naphthalene ring, etc.; W is an electron-withdrawing group having a positive Hammett sigma value and includes groups such as cyano, nitro, fluoro, chloro, bromo, iodo, trifluoromethyl, trialkylammonium, carbonyl, N-substituted carbamoyl, sulfoxide, sulfonyl, N-substituted sulfamoyl, ester and the like; $R^2$ is a hydrogen atom, a substituted or unsubstituted alkyl group preferably containing from 1–30 carbon atoms, or a substituted or unsubstituted aryl group preferably containing from 6–30 carbon atoms; $R^1$ is a bivalent organic group containing from 1–3 atoms in the bivalent linkage and can be alkylene groups, oxaalkylene, thioalkylene, aminoalkylene, alkyl- or aryl-substituted nitrogen atoms and the like; m and q are positive integers of 1 or 2; p is a positive integer of 1 or greater and preferably 3–4, with $[(R^2)_{\overline{q-1}}W]$ being a substituent on any portion of the aromatic ring structure of A, and p is 1 only when A contains an aromatic 'onium group, and when p is 2, $[(R^2)_{\overline{q-1}}W]$ is ortho or para to the nitro group on said formula; E and Q provide an electrophilic cleavage group where E is an electrophilic center and is preferably a carbonyl group including carbonyl (—CO—) and thiocarbonyl (—CS—) or it can be a sulfonyl group, and Q is a bivalent group providing a monoatom linkage between E and $X^1$ wherein said bivalent group can be an oxygen atom, a sulphur atom, a selenium atom, a nitrogen atom which provides an amino group and the like, and preferably Q is an amino group with an alkyl group substituent containing from 1–20 atoms and preferably from 1–10 carbon atoms, including substituted alkyl groups; n is an integer of 1–3 and is preferably 1; and $X^1$, together with Q, is either an image dye-providing material such as an image dye or an image dye-precursor or a photographic reagent such as an antifoggant moiety, a toner moiety, a fixing agent, a development accelerator, a developing-agent moiety, a hardener moiety, a development-inhibitor moiety and the like.

It is to be understood that, when multiple groups are present in the compound as designated in the above formula, they may be identical or different; for example, when p is 3, each $[(R^2)_{q-1}—W]$ may be selected from different substituents as specified, and it is understood that $R^2$ may be present on all or only some of said electron-withdrawing groups; i.e., when p is greater than 2, q can be 2 on some of the groups and 1 on some of the groups.

The formula above includes compounds where multiple cleavage groups are located on an image dye-providing material or a photographic reagent, i.e., when n is greater than 1. Compounds of this type are advantageous where more than one cleavable group is used to shift a dye, prevent reaction of the material or provide additional controls on the diffusion of a diffusible moiety.

In certain embodiments and especially those embodiments where the compounds are used in photographic elements, $R^2$ is preferably present in the compound as a ballasting group to render the compound immobile and nondiffusible under alkaline processing conditions and $(Q—X^1)$ represents a diffusible moiety. The nature of the ballasting group is not critical, as long as the portion of the compound on the ballast side of E is primarily responsible for the immobility. Generally, when $R^2$ is a ballast group, $R^2$ will comprise long-chain alkyl radicals, as well as aromatic radicals of the benzene and naphthalene series. Typical useful groups for the ballast function contain from 8–30 carbon atoms and preferably at least 12 carbon atoms.

The electron-withdrawing groups referred to for the compounds of the above formulae generally are those groups which have a positive Hammett sigma value and preferably a sigma value more positive than 0.2 or a combined effect of more than 0.5 as substituents of the aromatic ring. The Hammett sigma values are calculated in accordance with the procedures in *Steric Effects in Organic Chemistry,* John Wiley and Sons, Inc., 1956, pp. 570–574, and *Progress in Physical Organic Chemistry,* Vol. 2, Interscience Publishers, 1964, pp. 333–339.

Typical useful electron-withdrawing groups having positive Hammett sigma values include cyano, nitro, fluoro, bromo, iodo, trifluoromethyl, trialkylammonium, carbonyl, N-substituted carbamoyl, sulfoxide, sulfonyl, N-substituted sulfamoyl, esters and the like. Where the term "aromatic ring having an electron-withdrawing substituent" is used herein, it refers to 'onium groups in the ring and to those groups substituted directly on the ring which may be linkage for other groups such as ballast groups.

The electron-withdrawing groups include groups in the ring such as in a compound of the formula:

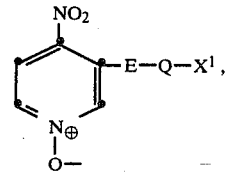

wherein E, Q and $X^1$ are as defined above.

Generally, the compounds of this invention are precursors for compounds which function in the photographic element as intramolecular nucleophilic displacement compounds. The nitro group on the compound undergoes reduction to form a nucleophilic group. The term "intramolecular nucleophilic displacement" is intended to refer to a mechanism where a portion of the molecule is actually displaced rather than merely relocated on the molecule; i.e., the electrophilic center must be capable of forming a ring structure with said nucleophilic group. In the compounds of the present invention, the nitro group on the aromatic ring becomes a nucleophilic group after it is reduced, i.e., after accepting at least one electron. Generally, the intramolecular nucleophilic displacement compounds are those compounds that have the nucleophilic group and the electrophilic center juxtaposed by the three-dimensional configuration of the molecule to promote close proximity of the groups whereby the intramolecular nucleophilic displacement reaction can take place. Generally, the respective eletrophilic and nucleophilic groups can be located in the compounds, including polycyclic compounds, where the groups are held in the possible reaction positions. However, the nucleophilic groups and electrophilic groups are preferably located on compounds wherein a cyclic organic ring or a transient cyclic organic ring can be easily formed by intramolecular reaction of the nucleophilic group at the electrophilic center. Cyclic groups can be generally formed with 3–7 atoms therein, and preferably in accordance with this invention the nucleophilic group and the electrophilic group are positioned on a compound where they can form a 5- to 7-membered ring, and more preferably a 5- or 6-membered ring (4-membered rings are generally known to be difficult to form in organic reactions). Intramolecular nucleophilic displacement occurs with the compounds of this invention after the nitro group has accepted at least one electron. The rate of nucleophilic displacement is very low or substantially zero prior to reduction of the nitro group.

It should be understood that the compounds of this invention are stable under the conditions of processing except where the primary cleavage of the compound occurs as a direct function of the reduction of a nitro group. The compound may contain other groups which ionize or hydrolyze, but the primary imagewise release occurs by intramolecular nucleophilic displacement where the nucleophilic group, provided by reduction of said aromatic nitro group, reacts with the electrophilic center of the cleavage group on the compound. It is understood that, where the aromatic nitro compounds are to be used in highly alkaline conditions, the various groups of the aromatic nitro compound are selected to provide compounds which are relatively stable to external attack by alkali.

Generally, the nitro group and the electrophilic group are both attached to the same aromatic ring structure, which can be a carbocyclic ring structure or a heterocyclic ring structure and includes fused rings wherein each group can be on a different ring; preferably, both groups are attached directly to the same aromatic ring, which is preferably a carbocyclic ring structure.

Generally, the intramolecular nucleophilic displacement compounds provided by reduction of the compounds of this invention contain from 3 to about 5 atoms and preferably 3 or 4 atoms between the nucleophilic center of the nucleophilic group and the atom which forms the electrophilic center, whereby the nucleophilic center, taken together with the center of the electrophilic group, is capable of forming a ring or a transient ring having from 5-7 atoms therein and preferably 5 or 6 atoms therein.

The term "nucleophilic group" as used herein refers to an atom or group of atoms that have an electron pair capable of forming a covalent bond. Groups of this type are sometimes ionizable groups that react as anionic groups. The compounds of this invention contain nitro groups which undergo reduction to provide a nucleophilic group such as an hydroxylamino group.

The hydroxylamino nucleophilic group can contain more than one nucleophilic center; i.e., either the nitrogen atom or the oxygen atom can be the nucleophilic center. Where more than one nucleophilic center is present in the nucleophilic group on the intramolecular nucleophilic displacement compounds of this invention, the nucleophilic attack and displacement will generally occur through the center which is capable of forming the most favored ring structure; i.e., if the oxygen atom of the hydroxylamino group would form a 7-membered ring and the nitrogen atom would form a 6-membered ring, the active nucleophilic center would generally be the nitrogen atom.

The term "electrophilic group" refers to an atom or group of atoms that are capable of accepting an electron pair to form a covalent bond. Typical electrophilic groups are sulfonyl groups (—$SO_2$—), carbonyl (—CO—) and thiocarbonyl (—CS—) and the like, where the carbon atom of the carbonyl group forms the electrophilic center of the roup and can sustain a partial positive charge. The term "electrophilic cleavage group" is used herein to refer to a group (—E—Q—) wherein E is an electrophilic group and Q is a bivalent leaving group providing a mono atom linkage between E and $X^1$ wherein said mono atom is a nonmetallic atom that has a negative valence of 2 or 3. The leaving group is capable of accepting a pair of electrons upon being displaced from the electrophilic group. Where the nonmetallic atom is a trivalent atom, it can be monosubstituted by a group which can be a hydrogen atom, an alkyl group including substituted alkyl groups and cycloalkyl groups, or an aryl group including substituted aryl groups. Typical atoms useful in Q are the nonmetallic atoms in groups VA and VIA of the periodic table which are capable of having a negative valence of 2 or 3, such as nitrogen atoms, sulfur atoms, oxygen atoms, selenium atoms and the like.

The compounds of the present invention include many types of dye-providing materials and photographic reagents that benefit from the cleavage in accordance with this invention. Immobile compounds can be prepared where the ballasting portion is cleaved from a diffusible moiety which can then diffuse to adjacent layers in a photographic element. A group can be cleaved from the compound to render the compound active, such as on a development inhibitor, or to shift the resonance such as on a shifted dye. In still other embodiments, the group can be cleaved to enable the compound to undergo subsequent reactions in the photographic element.

The compounds of the present invention offer several improvements over those known in the prior art. Generally, the compounds provide the advantage that they must accept electrons (undergo reduction) before any cleavage will occur. Meanwhile, the compound remains relatively stable in various liquid media such as alkaline solutions. In contrast, many related compounds must be oxidized before they will undergo cleavage or they hydrolyze to cleave the compound as a function of pH rather than as a function of reduction.

In most uses contemplated for the aromatic nitro compounds of this invention, they are reacted with an electron donor which reduces the nitro compound providing a nucleophilic group on the compound for the subsequent intramolecular nucleophilic displacement of the releasable moiety. The electron donor can be provided to the aromatic nitro compound by spraying, stencil, physical transfer, imbibition, imagewise transfer, etc. The term "electron-donor" is understood to include those compounds or materials which are capable of reducing the aromatic nitro compounds of this invention.

The aromatic nitro compounds can be used in combination with organic electron donors in photographic elements. In a photographic element containing a layer of silver halide having an aromatic nitro compound associated therewith, the electron donor is destroyed as a function of silver halide development. In the remaining areas, the electron donor reduces the aromatic nitro compound whereby intramolecular nucleophilic displacement can take place. Where the electron donor is also a good silver halide developer, an electron donor is used which has a faster reaction rate with the silver halide than it does with the aromatic nitro compound. Typical useful electron donors which are also silver halide developers include ascorbic acid, trihydroxypyrimidines such as 2-methyl-4,5,6-trihydroxypyrimidine, hydroxylamines such as diethyl hydroxylamine, and the like.

The aromatic nitro compounds of this invention can also be used in photographic elements in combination with organic electron donors which are relatively poor silver halide developers or do not develop silver halide, as disclosed by Chasman, Dunlap and Hinshaw, U.S. Ser. No. 775,025 entitled PHOTOGRAPHIC ELEMENTS CONTAINING BALLASTED ELECTRON-ACCEPTING NUCLEOPHILIC DISPLACEMENT COMPOUNDS, filed Mar. 7, 1977, now U.S. Pat. No. 4,139,379 issued Feb. 13, 1979 and which is incorporated herein by reference. The electron donors can be present in the photographic element as a hydrolyzable precursor for the electron donor, an immobile electron donor or a diffusible electron donor. Generally, the electron donor is destroyed imagewise, and where it has not been destroyed it reacts with the aromatic nitro compound to transfer electrons whereby the aromatic nitro compound can undergo cleavage. In one embodiment in a photographic element, the aromatic nitro compounds are used in combination with a substantially immobile hydrolyzable electron-donor precursor and an electron-transfer agent. The electron transfer agent, such as a 3-pyrazolidone compound, reacts with developable silver halide to provide oxidized electron-transfer agent. The oxidized electron transfer agent reacts with the electron donor as it is made available by hydrolysis to destroy an imagewise pattern of the electron donor. The remaining electron donor can react with the aromatic nitro compound whereby it can undergo cleavage. Where a diffusible dye is released, it will be made available for diffusion to an adjacent image-receiving layer.

Alkali-labile electron donors which are preferably used according to Chasman, Dunlap and Hinshaw, supra, include those compounds which have a finite rate of hydrolysis under processing conditions and include benzisoxazolones, lactones, blocked hydroquinones and the like.

Typical electron donors which can be used in combinations with the aromatic nitro compounds of this invention include:

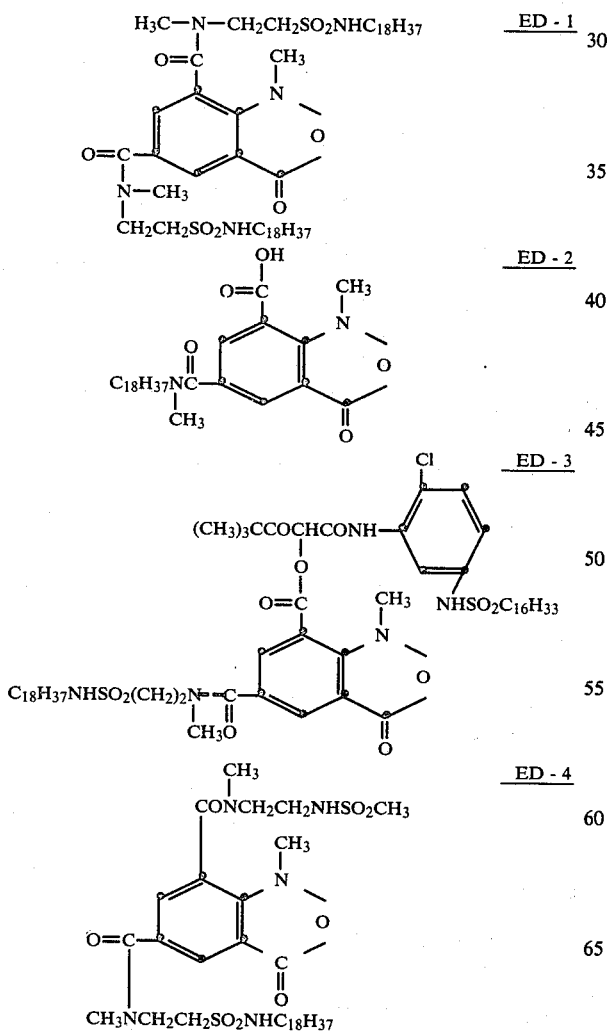
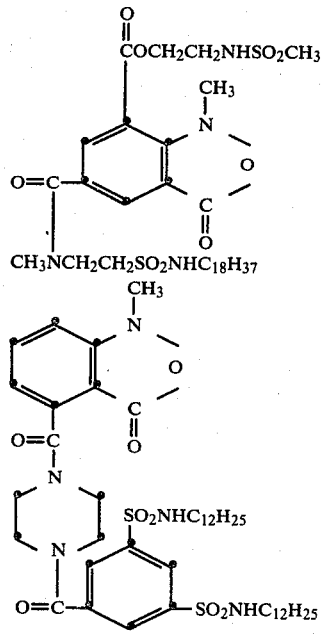
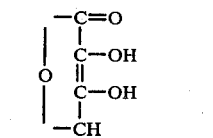
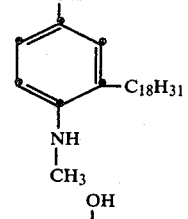
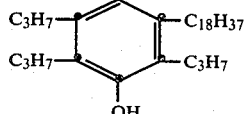

In certain preferred embodiments, the cleavable group is used as a substituent on a shiftable dye to control the resonance of the dye. Upon cleavage of the aromatic nitro group from the dye, it will undergo a bathochromic or hypsochromic shift. Shiftable dyes are generally known in the prior art, including those disclosed by Weyerts, U.S. Pat. No. 3,260,597 issued July 12, 1966, wherein an acyl group is used to shift the absorption of the dye. Generally, the cleavage moieties of the present invention can be used on and dye where there is an ionizable nitrogen atom, oxygen atom, sulfur atom or selenium atom which affects the resonance of the dye. In accordance with this invention, the cleavable moiety is substituted on the dye so that the ionizable group is the leaving group in the electrophilic cleavage group.

The moiety represented by $+Q-X^1)$ in the above formula can be a silver halide development inhibitor including triazoles and tetrazoles such as a 5-mercapto-1-phenyltetrazole, a 5-methylbenzotriazole, a 4,5-dichlorobenzotriazole and the like, and it can also be an antifoggant including azaindenes such as a tetrazaindene and the like. The compounds that contain releasable silver halide development inhibitors or antifoggants can generally be used in the photographic elements in association with silver halide layers wherein said compound can be incorporated in amounts such as 0.1 to 3.0 mg./m.$^2$ dissolved in a coupler solvent such as diethyl lauramide. When these compounds are incorporated in photographic elements in association with negative silver halide emulsions, a positive imagewise distribution of inhibitor or antifoggant will be produced upon development. Thus, silver development is inhibited or restrained in the low-exposure toe as seen on the Density/Log E curve, but not in the more fully exposed shoulder as seen on the Density/Log E curve. Development inhibition of the unexposed areas is thereby achieved selectively. When the silver halide emulsions also have dye releasers in accordance with this invention associated therewith, the overall effect of the inhibitor or antifoggant is to release more dye in the unexposed regions, improving maximum image dye density to the image-receiving layer without increasing the amount of dye released in the exposed regions.

In certain preferred embodiments, cleavable groups of this invention are used to ballast a moiety which is a diffusible dye-providing material. Preferably, the image dye-providing moiety is a preformed dye or a shifted dye. Dye materials of this type are well-known in the art and include dyes such as azo dyes including metallizable azo dyes and metallized azo dyes, azomethine ((imine) dyes, anthrquinones dyes, alizarin dyes, merdcyanine dyes, quinoline dyes, cyanine dyes and the like. The shifted dyes include those compounds wherein the light absorption characteristics are shifted hypsochromically or bathochromically when subjected to a different environment such as a change in pH, reaction with a material to form a complex such as with a metal ion, removal of a group such as a hydrolyzable acyl group connected to an atom of the chromophore as mentioned by Weyerts, U.S. Pat. No. 3,260,597 issued July 12, 1966, and the like. The electrophilic cleavage group and other groups on the molecule should, of course, be selected to provide stable compounds when used under highly alkaline conditions, and preferably the cleavable moiety is attached to an amino group when the compound is used under highly alkaline conditions. In certain embodiments, the shifted dyes are highly preferred and especially those containing a hydrolyzable group on an atom affecting the chromophore resonance structure, because the compounds can be incorporated directly in a silver halide emulsion layer or even on the exposure side thereof without substantial reduction in the recording light exposure. After exposure, the dye can be shifted to the appropriate color such as, for example, by hydrolytic removal of the acyl group to provide the respective image dye.

In another embodiment, the cleavage groups of this invention are used to provide a temporary ballast on a moiety which is a diffusible image-dye precursor. The term "image-dye precursor" is understood to refer to those compounds that undergo reactions encountered in a photographic imaging system to produce an image dye, such as color couplers, oxichromic compounds, and the like.

The aromatic nitro compounds described herein have particular application in a photographic process where it is desired to have a diffusible entity such as a dye transferred to an adjacent layer or a receiving element. However, in certain embodiments this invention relates to the release of an imagewise distribution of a diffusible photographically useful compound which is a photographic reagent. Typical useful photographic reagents are known in the art, such as in U.S. Pat. Nos. 3,227,551, 3,698,898, 3,379,529 and 3,364,022, for example, a silver complexing agent, a silver halide solvent, a fixing agent, a toner, a hardener, an antifoggant, a fogging agent, a sensitizer, a desensitizer, a developer or an oxidizing agent. In other words, —Q—X$^1$ in the above formula may represent any moiety which, in combination with a hydrogen atom, provides a photographic reagent upon cleavage.

Typical useful photographic reagents containing the cleavage group according to this invention are as follows:

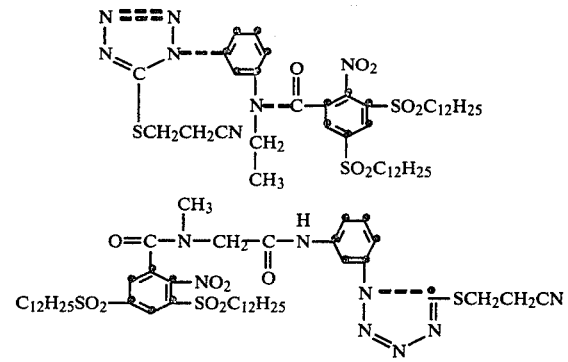

The diffusible moiety represented by Q—X$^1$ can also be a silver halide development accelerator such as a benzyl alcohol, a benzyl α-picolinium bromide and the like, a fogging agent or nucleating agent, or an auxiliary developer such as a 1-phenyl-3-pyrazolidone, and the like. When these compounds are used in photographic elements in association with silver halide emulsions which also have associated therewith image dye-providing materials in accordance with this invention, the released dye density of all dyes in the unexposed regions would be somewhat reduced by fog development. If, however, one layer was unexposed while the other two were given an imagewise exposure, the amount of fogant or development accelerator reaching the unexposed layer from the other two layers would be less where those layers were exposed. Hence, the Dmax of the unexposed layer would increase as a function of exposure of the other two layers. This greatly enhances the saturation of single colors in a photograph.

When color couplers are present in the compounds of this invention, the couplers can be released or made available in areas where no development occurs and can be reacted with an oxidized color developer such as a primary aromatic amine to form the image dye. Generally, the color coupler and the color developer are so chosen that the reaction product is immobile. Typical useful color couplers include the pyrazolone couplers, pyrazolotriazole couplers, open-chain ketomethylene couplers, phenolic couplers and the like. Further reference to the description of appropriate couplers is found in U.S. Pat. No. 3,620,747 by Marchant issued Nov. 16, 1971, which is incorporated herein by reference.

The compounds of this invention containing oxichromic moieties can also be advantageously used in a photographic system because they are generally colorless materials due to the absence of an image-dye chromophore. Thus, they can also be used directly in the photographic emulsion or on the exposure side thereof without competitive absorption. Compounds of this type are those compounds which undergo chromogenic oxidation to form the respective image dye. The oxidation can be carried out by subsequent aerial oxidation or incorporation of oxidants into the imagereceiving layers of the film unit. Compounds of this type have been referred to in the art as leuco compounds, i.e., compounds which have no color. Typical useful oxichromic compounds include leuco indoanilines, leuco indophenols, leuco anthraquinones and the like. In certain preferred embodiments, the compounds of this invention contain oxichromic moieties as described by Lestina and Bush, U.S. Pat. No. 3,880,658, which is incorporated herein by reference.

In those embodiments of this invention where the aromatic nitro compounds contain an image dye-providing moiety, they are generally used in a layer on a support in sufficient quantity to produce a discernible image record. The concentration needed will depend on the thickness of the layer and absorption characteristics of the dye. However, where a visible image record is desired, the aromatic nitro compound is generally used in concentrations of at least $1 \times 10^{-5}$ moles/m.$^2$ and preferably from about $1 \times 10^{-4}$ to $2 \times 10^{-3}$ moles/m.$^2$.

The compounds of this invention are particularly useful in photographic elements and in photographic processes to provide an imagewise distribution of a photographically useful compound. The photographic element can contain the immobile compounds in association with any photographic material that produces an imagewise distribution of electron donor during development which in turn can react with the nucleophile precursor group on said aromatic nitro compound. In certain preferred embodiments, where silver halide emulsions are used as the recording means, the emulsion can be a negative, direct-positive or reversal emulsion and the like which undergo development with a silver halide developing agent to produce oxidized silver halide developer. The unexhausted silver halide developing agent can react with the nucleophile precursor group by a simple redox reaction or electron transfer to provide the nucleophilic group, whereby intramolecular nucleophilic displacement of the diffusible moiety can take place.

Black-and-white or one-color systems can be made that employ as few as one silver halide emulsion and compounds according to this invention that comprise the required image dye-providing moieties to provide the desired net color effect. Preferably, the compounds of this invention are used in three-color systems such as, for example, photographic elements containing a layer comprising a red-sensitive silver halide emulsion having associated therewith an aromatic nitro compound comprising a cyan image dye-providing moiety, a layer containing a green-sensitive silver halide emulsion having associated therewith an aromatic nitro compound that comprises a magenta image dye-providing moiety, and a layer containing a blue-sensitive silver halide emulsion having associated therewith an aromatic nitro compound that comprises a yellow image dye-providing moiety.

The photographic element can be designed to provide an image record in either the image dye-providing material released and made diffusible or the immobile dye retained in the initial location associated with the respective photographic recording material or, in certain instances, both image records can be used. Where the retained image is used, the silver and silver halide remaining after development can be removed, if desired, to provide better color properties in the record.

The photosensitive substances used in the photographic elements of this invention are preferably silver halide compositions and can comprise silver chloride, silver bromide, silver bromoiodide, silver chlorobromoiodide and the like, or mixtures thereof. The emulsions may be coarse- or fine-grain and can be prepared by any of the well-known procedures, e.g., single-jet emulsions, double-jet emulsions, such as Lippmann emulsions, ammoniacal emulsions, thiocyanate or thioether ripened emulsions such as those described in U.S. Pat. Nos. 2,222,264 by Nietz et al, 3,320,069 by Illingsworth and 3,271,157 by McBride. Surface-image emulsions can be used or internal-image emulsions can be used such as those described in U.S. Pat. Nos. 2,592,250 by Davey et al, 3,206,313 by Porter et al and 3,447,927 by Bacon et al. The emulsions may be regular-grain emulsions such as the type described by Klein and Moisar, *J. Phot. Sci.*, Vol. 12, No. 5, Sept./Oct., 1964, pp. 242-251. The silver halide emulsions can be spectrally sensitized by means known in the art including techniques of spectrally sensitizing to provide good color balance under various light illumination as described by Schwan et al, U.S. Pat. No. 3,672,898 issued June 27, 1972. Silver halide emulsions made using techniques well-known in the art to achieve high-camera speed, such as having ASA speeds of from 400 to above 1000, are especially useful in this invention.

Blends of emulsion having different grain sizes and/or sensitivities can be used to control contrast and exposure latitude. Such emulsions can also be coated in separate layers, if desired, with an image dye-providing material in one or more of such emulsions, especially when preformed dyes are used.

Negative-type emulsions can be used or directpositive emulsions can be used such as those described in U.S. Pat. Nos. 2,184,013 by Leermakers, 2,541,472 by Kendall et al, 3,367,778 by Berriman, 3,501,307 by Illingsworth et al issued Mar. 17, 1970, 2,563,785 by Ives, 2,456,953 by Knott et al, 2,861,885 by Land, 3,761,276 by Evans, 3,761,266 by Milton, 3,761,267 by Gilman et al, 3,736,140 by Collier et al and 3,730,723 by Gilman et al, British Pat. No. 723,019 by Schouwenaars, and U.S. Ser. No. 154,155 by Gilman et al filed June 17, 1971 now abandoned and reflied as U.S. Ser. No. 398,906 on Sept. 19, 1973, also abandoned and refiled as U.S. Ser. No. 554,932 on Mar. 3, 1975 and issued as U.S. Pat. No. 4,011,081.

In still another embodiment, the aromatic nitro compounds can be coated in a layer in an alkali-permeable binder on a support to provide what is often referred to as a receiver element. The receiver element can be processed by several methods including positioning it in interfacial contact with a photographic silver halide element in the presence of an alkaline solution and a silver halide developer. In those areas where an electron donor such as unexhausted silver halide developer diffuses to the receiver layer, the aromatic nitro compound will be reduced, and if it contains a dye moiety it will provide a permanent image dye record in the areas corresponding to the original silver halide development. The remainder of the diffusible dye can be removed from the element, for example, by washing, after intramolecular nucleophilic displacement. With proper selection of the image dye-providing moieties, a black-and-white image can be obtained. Also, if the nucleophilic compound contains a tanning agent as the photographically useful moiety, it is possible to obtain a tanned image record in areas where silver halide development does not take place, i.e., a positive image record if a negative emulsion is used.

In still other embodiments, compounds of this invention can be uniformly coated on a supporting material. When the distribution of the compound is contacted with imagewise patterns of an electron donor and held under conditions which promote intramolecular nucleophilic displacement, an imagewise pattern of the cleaved material will be obtained. In instances where the compound is a shiftable dye containing the cleavage moiety where it shifts the absorption, an imagewise pattern having a bathochromic shift in absorption or a hypsochromic shift will be made available by cleavage. The imagewise pattern of electron donor can be provided by stencil, rubber stamp, spraying, dropwise distribution, etc.

In still other embodiments, the compounds of this invention can be used to determine the presence of and the quantity of certain reducing agents in a given medium.

In still other embodiments, the compounds of the present invention can be used in a stepwise process where they are reduced in the first step where they may be visibly unchanged. Subsequent contact with an alkali medium will promote intramolecular nucleophilic displacement where reduction has occurred.

The term "nondiffusing" used herein has the meaning commonly applied to the term in photography and denotes materials that for all practical purposes do not migrate nor wander through organic colloid layers in an alkaline medium, such as gelatin, in the photographic elements of the invention and preferably do not wander nor migrate in an alkaline medium having a pH in excess of 11. The same meaning is to be attached to the term "immobile". The term "diffusible" as applied to the materials of this invention has the converse meaning and denotes materials having the property of diffusing effectively through the colloid layers of the photographic elements in an alkaline medium in the presence of "nondiffusing" materials. "Mobile" has the same meaning.

In those embodiments where the aromatic nitro compounds are used in the layers of photographic elements, they can be incorporated by any means known in the art. Generally, where high-molecular-weight, ballasted, aromatic nitro compounds are incorporated in alkali-permeable hydrophilic colloids, the compounds can be dispersed in any convenient manner, such as using solvents and techniques described in U.S. Pat. Nos. 2,322,027 by Jelley issued June 15, 1943, or 2,801,171 by Fierke et al issued June 30, 1957. When coupler solvents are employed, the most useful range of aromatic nitro compound to coupler solvent is from 1:3 to 0.1. Preferably, the coupler solvent is a moderately polar solvent. Typical useful solvents include tri-o-cresyl phosphate, di-n-butyl phthalate, diethyl lauramide, 2,4-diamylphenol, liquid dye stabilizers as described in an article entitled "Improved Photographic Dye Image Stabilizer-Solvent", *Product Licensing Index,* Vol. 83, pp. 26-29, March, 1971, and the like. In other embodiments, the aromatic nitro compounds can be dissolved in a water-miscible organic solvent such as tetrahydrofuran, methyl alcohol, ethyl alcohol, isopropyl alcohol, acetone, 2-butanone, N-methylpyrrolidone, dimethylformamide, dimethyl sulfoxide or mixtures thereof, and to this mixture can then be added a suitable loadable polymeric latex of the type disclosed by Chen, German OLS No. 2,541,274, where the compounds are distributed on the latex particles.

In this application, certain groups are identified with reference to the periodic table. The reference table is located on pp. 400-401 of the *Handbook of Chemistry and Physics,* 39th Ed., Chemical Rubber Publishing Co.

The photographic elements, as described above, generally comprise at least one layer containing photographic recording material, such as silver halide, having associated therewith an immobile compound. The term "associated therewith" is a term of art in the photographic industry and generally refers to said immobile compound in alkaline-permeable relationship with said photographic recording material. The respective materials can be coated in the same layers or separate layers, as long as they are effectively associated and isolated to provide for the desired reactions before a substantial amount of the intermediate reactant products diffuse into adjacent photographic recording layers, etc.

Typical compounds of the invention and their preparation are disclosed in the following examples. The releasable fragments described are typical mobile dyes useful in photography.

In the synthesis of the compounds in the following examples, the structure was confirmed in each instance by infrared analysis and, in some instances, further verified by nmr and mass spectroscopy analysis. Melting points for the intermediates are specified where they were applicable in further identification of the respective compound.

EXAMPLE 1

Compound I

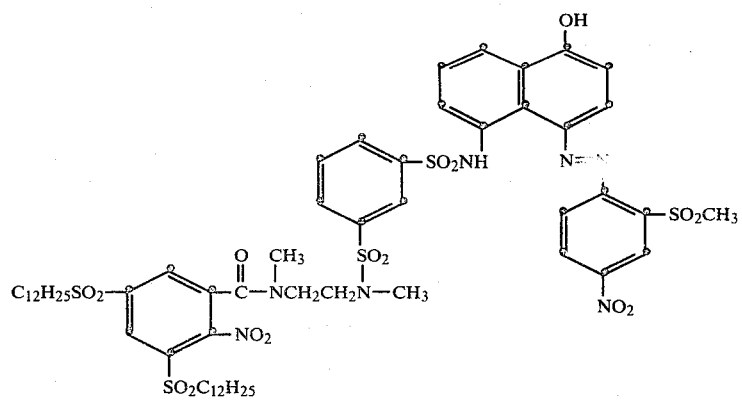

Step 1: 3,5-dichloro-2-nitrobenzoic acid

In a 5-liter, 3-necked flask were placed 2000 ml. of 90% nitric acid. The mixture was stirred and heated to 70° C. The heating mantel was removed and, with continued stirring, 500 g. of solid 3,5-dichlorobenzoic acid was added in portions so as to maintain a reaction temperature of about 70° C. (The addition is only very mildly exothermic so that large portions of the dichloroacid may be added at one time. The total time for addition of the 500 g. was about 20 min.) After the addition, the reaction was stirred and heated at 75°–80° C. for 3 hr. The mixture (containing some solid) was then cooled, finally in ice. The solid was collected on a sintered glass funnel and washed with cold water (3×500 ml.) and dried. Yield 555.3 g. (90%); m.p. 190°–192° C.

Step 2: 3,5-didodecylthio-2-nitrobenzoic acid

An amount of 236 g. (1 mole) 3,5-dichloro-2-nitrobenzoic acid (Step 1) and 424 g. (2.1 moles) 1-dodecanethiol in 1.5 liter ethanol and 1 liter water was purged with nitrogen for 15–30 min. Then 430 g. (3.1 moles) anhydrous potassium carbonate were added and the reaction mixture was refluxed under an atmosphere of nitrogen for 60–72 hr. After cooling to room temperature, the solution was poured slowly into a rapidly stirred mixture of 6 liters water, 360 ml. conc. HCl and crushed ice. The precipitated solid was collected and washed well with water. The yellow material was slurried in 2.7 liters of glacial acetic acid, filtered, washed with a small amount of glacial acetic acid and dried in vacuo at 45° C. An amount of 560 g. of the product was obtained, m.p. 74°–77° C.

Step 3: 3,5-didodecylsulfonyl-2-nitrobenzoic acid

To a stirred slurry of 320 g. (0.56 mole) 3,5-didodecylthio-2-nitrobenzoic acid (Step 2) and 0.6 g. (0.002 mole) (ethylenedinitrilo)tetraacetic acid in 2.6 liters glacial acetic acid were added 330 ml. of 30% hydrogen peroxide. The mixture was heated gradually to 75° C. when a mild exotherm (to about 90° C.) began. Heating was stopped until the exotherm subsided. Then the run was heated at 80° C. until a negative or very weak test for peroxide was obtained with starch-iodide paper. At this point, 70 ml. of 30% hydrogen peroxide were added all at once and heating at 80° C. was resumed for about 15 hr. Cooling crystallized the desired white crystals which were collected and washed in sequence with cold glacial acetic acid and then water. On drying, 340 g. of product were obtained, m.p. 153°–154.5° C.

Step 4: 3,5-didodecylsulfonyl-2-nitrobenzoyl chloride

Oxalyl chloride (2 ml., 0.16 mole), followed by 2 drops of N,N-dimethylformamide (DMF), was added to a slurry of 6.32 g. (0.01 mole) 3,5-didodecylsulfonyl-2-nitrobenzoic acid (Step 3) in 50 ml. benzene. When the initial rapid evolution of gas had subsided, 6 drops of DMF were added in two portions. After 1 hr., an additional 1 ml. oxalyl chloride was added. The reaction mixture was concentrated to a yellow paste and then was titurated with about 50 ml. cold acetonitrile. The mixture was filtered and washed with fresh acetonitrile to give a white solid. After drying in a vacuum oven, 4.81 g. (74% yield) of the desired acid chloride were obtained.

Step 5: Compound I

A solution of 5.2 g. (0.008 mole) of acid chloride (Step 4 above) in 30 ml. tetrahydrofuran (THF) was added dropwise to a stirred solution of 5.7 g. (0.008 mole) of 5-{3-[N-(methylaminoethyl)-N-methylsulfamoyl]phenylsulfonamido}-4-(2-methylsulfonyl-4-nitrophenylazo)-1-naphthol hydrochloride (dye fragment A) in 50 ml. DMF containing 1.7 g. (0.0176 mole) triethylamine. After the addition, most of the THF was removed under vacuum. The remaining solution was poured slowly with rapid stirring into 250 ml. ice-cold water. The deep blue-black solid was collected and washed in sequence with water, dilute (0.01 N) HCl, and then water. The washed material was dried, dissolved in THF and added to a 2-inch-by-8-inch column filled with 100–200 mesh Florisil (activated magnesium silicate). The product was eluted with 1500 ml. THF. The eluate was concentrated to dryness. The residue was dissolved in a minimum of dichloromethane and then poured into 150 ml. of ice-cold ligroine (b.p. 35°–60° C.). The solid was collected, washed with ligroine and dried. A yield of 5.6 g. (54% yield) of Compound I was obtained.

EXAMPLE 2

Compound II

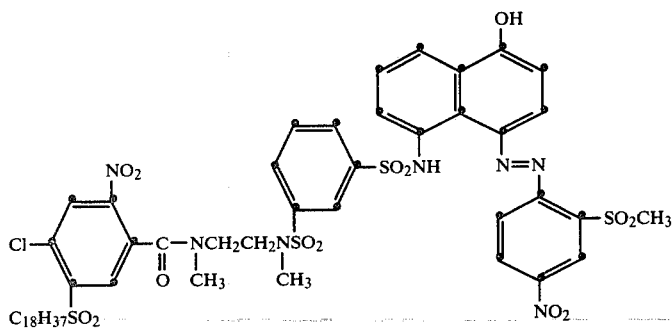

Step 1: 4-chloro-5-octadecylsulfonyl-2-nitrobenzoic acid

This compound was prepared from 4,5-dichloro-2-nitrobenzoic acid in the manner described in Example 1, Steps 2 and 3, using one equivalent of octadecanethiol in place of dodecanethiol.

Step 2: 4-chloro-5-octadecylsulfonyl-2-nitrobenzoyl chloride

This compound was prepared from the free acid (Step 1 above) and 16 equivalents of oxalyl chloride according to the procedure of Example 1, Step 4.

Step 3: Compound II

The corresponding dye-containing compound was prepared by following the procedure described in Step 5 of Example 1 using dye fragment A and 4-chloro-5-octadecylsulfonyl-2-nitrobenzoyl chloride prepared in Step 2 above.

A number of other nitrobenzenoid derivatives and dye fragments were prepared and reacted together to form various other aromatic nitro compounds of the invention. Typical reactions and conditions for making these compounds are described in Examples 1 and 2 above. The alkylenediamino group linking the dye to the nitrobenzoic acid was supplied either by (1) reacting the corresponding monoprotected diamine with the appropriate ballasted nitrobenzoyl chloride, followed by deprotection of the amine and reaction with a dye fragment bearing a sulfonyl chloride group, or (2) by reacting an excess of a diamine with a dye fragment containing a chlorosulfonyl group and reacting the resulting amine dye with the appropriate ballasted nitrobenzoyl chloride. Compounds were prepared using two types of nitro derivatives and the appropriate types of dye fragments as shown in Table 1 below.

Table 1

| Example | Compound | Nitrobenzenoid Derivative | Dye Fragment |
|---|---|---|---|
| 3 | III | $C_{12}H_{25}SO_2$-, $NO_2$, -COCl, $SO_2C_{12}H_{25}$ | OH, $CH_3SO_2NH$, N=N, $-SO_2NC_2CH_2NH \cdot HCl$ ($CH_3$, $CH_3$) |
| 4 | IV | $C_{12}H_{25}SO_2$-, $NO_2$, -COCl, $SO_2C_{12}H_{25}$ | CN, HO-, N=N, $HCl \cdot HNCH_2CH_2-N-SO_2$ ($CH_3$, $CH_3$) |
| 5 | V | $C_{12}H_{25}SO_2$-, $NO_2$, -C(=O)-N, -$CH_2$, $NH_2 \cdot HCl$, $SO_2C_{12}H_{25}$ | CN, D, N=N-, -OC(=O)-, $SO_2Cl$ |

Table 1-continued

| Example | Compound | Nitrobenzenoid Derivative | Dye Fragment |
|---|---|---|---|
| 6 | VI | [structure: 2-nitro-3,5-bis(dodecylsulfonyl)benzoyl-N-methyl-N-(3-aminopropyl)amide · HCl] | D |
| 7 | VII | [structure: 2-nitro-3,5-bis(octylsulfonyl)benzoyl chloride] | A (see Step 5 of Example 1) |
| 8 | VIII | same | C |
| 9 | IX | [structure: 2-nitro-5-octadecylsulfonylbenzoyl chloride] | A |
| 10 | X | [structure: 2-nitro-3-octadecylsulfonylbenzoyl chloride] | A |
| 11 | XI | [structure: 2-nitro-3,5-bis(dodecylsulfonyl)benzoyl-N-methyl-N-(3-aminopropyl)amide · HCl] | E [naphthalene dye structure with O-CO-$C_6H_5$, $SO_2NHC(CH_3)_3$, $NHSO_2CH_3$, N=N-$C_6H_4$-$SO_2Cl$] |

EXAMPLE 12:
Preparation of Compound XII

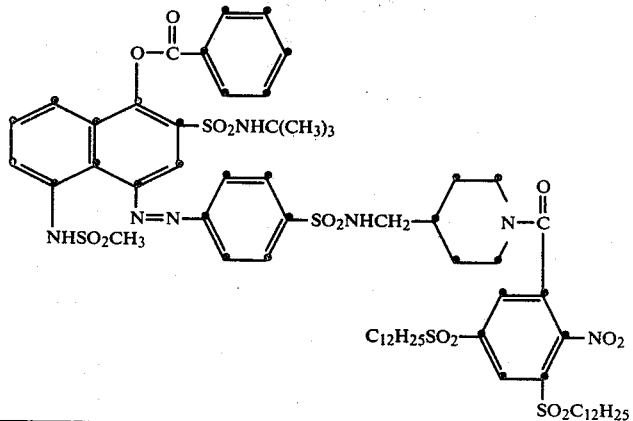

Step 1:
4-aminomethyl-1-(3,5-didodecylsulfonyl-2-nitrobenzoyl)piperidine hydrochloride To 1.14 g. (0.01 mole) of 4-aminomethylpiperidine in 25 ml. benzene were added 1.22 g. (0.01 mole) salicylaldehyde dropwise with stirring. The volume was then reduced to about 10 ml. by distilling off benzene at atmospheric pressure. The concentrated yellow solution was mixed with 30 ml. of tetrahydrofuran (THF) and 1.01 g. (0.01 mole) of triethylamine were added. The mixture was stirred and cooled in a cold-water bath while a solution of 6.5 g. (0.01 mole) of 3,5-didodecylsulfonyl-2-nitrobenzoyl chloride (see Example 1) in 40 ml. THF was added dropwise. After the addition, the reaction mixture was stirred for 30 min. at ambient temperature and filtered to remove the by-product, triethylamine hydrochloride. The solid was washed with a small amount of THF and discarded. The combined filtrate-and-THF wash was treated with 4 ml. 6 N HCl and stirred about 15 hr. The resulting gelled solution was boiled to reduce the volume of the acidified filtrate to about 50 ml. At this point, the hot solution was diluted slowly with 75 ml. acetonitrile and rapid stirring. The diluted mixture was stirred at ambient temperature until cool. The white solid was collected on a funnel, washed with cold acetonitrile and dried. The yield of the desired product was 4.69 g. TLC of a sample of the product on silica gel with methanol-acetone (5:20) gave only one spot.

Step 2: Compound XII

With stirring, 15.3 g. of 4-aminomethyl-1-(3,5-didodecylsulfonyl-2-nitrobenzoyl)piperidine hydrochloride were added to 300 ml. THF. After almost all of the hydrochloride had dissolved, 13.6 g. of 4-[4-benzoyloxy-8-methanesulfonamido-3-(N-t-butylsulfamoyl)-1-naphthylazo]benzenesulfonyl chloride were added, followed by dropwise addition of 4.0 g. of triethylamine. The viscosity of the mixture gradually decreased and stirring was continued for 4 hr. at ambient temperature. The run was filtered and the collected solid discarded. The filtrate was chromatographed on 500 g. Florisil, eluting with benzene-ethyl acetate (2:1). Crude product amounting to 18 g. was obtained from the elu- ate. This material was dissolved in 100 ml. ethyl acetate, filtered, diluted to 450 ml. volume with ether and allowed to stand about 15 hr. The solid that had formed was collected on a funnel, washed with a mixture of ethyl acetate and ether (1:3.5) and dried under vacuum at ambient temperature. The yield of Compound XII was 13.5 g.

EXAMPLES 13–15

The following compounds were prepared using a procedure similar to Example 12 with the appropriate intermediate materials.

Table 2

| Example | Compound |
|---------|----------|
| 13 | XIII |
| 14 | XIV |
| 15 | XV |

EXAMPLE 16

One-color Element with Nitro-substituted Compound and Incorporated Electron Donor A photographic image-transfer-type film unit was prepared by coating layers as follows:
Layer 1—polyethylene terephthalate film support;
Layer 2—a negative-type silver bromide emulsion (0.8μ) at 1.08 g. Ag/m.$^2$, gelatin at 1.61 g./m.$^2$, Compound VII at 0.44 g./m.$^2$, diethyl lauramide at 1.18 g./m.$^2$; and Electron Donor ED-1 at 0.74 g./m.$^2$; and
Layer 3—hardened gelatin at 0.54 g./m.$^2$.

A sample of the element was exposed through a graduated-density test object and processed by rupturing a pod containing a processing composition comprising 85 g. potassium hydroxide, 20 g. potassium bromide, 3 g. 4-methyl-4-hydroxymethyl-1-phenyl-3-pyrazolidone, 1.0 g. 5-methylbenzotriazole and 40 g. carboxymethyl cellulose per liter of water while in contact with a receiving element containing 2.15 g./m.$^2$ of copoly(styrene-co-N,N,N-tri-n-hexyl-N-vinylbenzyl ammonium chloride) and gelatin at 2.15 g./m.$^2$.

After 10 min., the photosensitive element and the receiver were separated and a well-defined positive cyan dye image (Dmax 2.0, Dmin 0.18) was observed in the receiver.

EXAMPLE 17

Another one-color photographic image-transfer-type film unit was prepared like Example 16, except that Electron Donor ED-2 at 0.27 g./m.$^2$ was used in place of Electron Donor ED-1 at 0.74 g./m.$^2$ and the amount of diethyl lauramide was reduced to 0.71 g./m.$^2$ instead of 1.18 g./m.$^2$.

A sample of the element was imagewise-exposed and processed according to the procedure described in Example 16.

After 5 min., the elements were separated and a well-defined cyan dye image (Dmax 1.28, Dmin 0.18) was observed in the receiver.

EXAMPLE 18

One-color nitro-substituted compound with electron donor in the processing composition A photographic image-transfer-type element was prepared having the following structure:
Layer 1—polyethylene terephthalate film support;
Layer 2—a silver bromide emulsion (0.8μ) at 1.08 g. Ag/m.$^2$, gelatin at 1.61 g./m.$^2$, Compound VII at 0.44 g./m.$^2$, and diethyl lauramide at 0.44 g./m.$^2$; and
Layer 3—hardened gelatin at 0.51 g./m.$^2$.

A sample of the element was exposed through a graduated-density test object and processed by rupturing a pod containing a processing composition comprising 51 g. potassium hydroxide, 20 g. potassium bromide, 0.5 g. 4-methyl-4-hydroxymethyl-1-phenyl-3-pyrazolidone, 3.0 g. N-methyl-5,7-dicarboxy-2,1-benzisoxazolone and 40 g. of carboxymethylcellulose per liter of water while in contact with a receiving element as described in Example 16.

After 5 min., the elements were separated and a well-defined positive cyan dye image (Dmax 1.01, Dmin 0.30) was observed in the receiver.

EXAMPLE 19

Three-color element with nitro-substituted compounds and incorporated electron-donor precursors A multilayer, multicolor image-transfer-type photographic element was prepared having the following structure:
Layer 1—a cellulose acetate film support;
Layer 2—a red-sensitive silver bromoiodide emulsion (0.8μ) at 1.08 g. Ag/m.$^2$, gelatin at 2.15 g./m.$^2$, Compound I at 0.42 g./m.$^2$, Electron Donor ED-1 at 0.63 g./m.$^2$ and 2,4-di-n-amylphenol at 1.05 g./m.$^2$;
Layer 3—gelatin at 1.61 g./m.$^2$, a magenta filter dye at 0.32 g./m.$^2$, 2,5-di-sec-dodecylhydroquinone at 0.22 g./m.$^2$ and diethyl lauramide at 0.16 g./m.$^2$;
Layer 4—a green-sensitive silver bromoiodide emulsion (0.8μ) at 1.61 g. Ag/m.$^2$, gelatin at 3.22 g./m.$^2$, Compound XII at 0.70 g./m.$^2$, Electron Donor ED-1 at 1.27 g./m.$^2$ and 2,4-di-n-amylphenol at 1.97 g./m.$^2$;
Layer 5—gelatin at 2.15 g./m.$^2$, a yellow filter dye at 1.08 g./m.$^2$, 2,5di-sec-dodecylhydroquinone at 0.22 g./m.$^2$ and diethyl lauramide at 0.54 g./m.$^2$;
Layer 6—a blue-sensitive silver bromoiodide emulsion (0.8μ) at 1.61 g. Ag/m.$^2$, gelatin at 3.22 g./m.$^2$, Compound VI at 0.58 g./m.$^2$, Electron Donor ED-1 at 1.32 g./m.$^2$ and 2,4-di-n-amylphenol at 1.89 g./m.$^2$; and
Layer 7—hardened gelatin at 0.86 g./m.$^2$.

A sample of the element was exposed with a white light source and selectively filtered light sources consisting of red, green, blue, cyan, magenta and yellow, each focused on a separate portion of the element.

The exposed sample was processed by rupturing a pod containing 51 g. potassium hydroxide, 20 g. potassium bromide, 3.0 g. 4-methyl-4-hydroxymethyl-1-phenyl-3-pyrazolidone, 2.0 g. 5-methylbenzotriazole and 40 g. carboxymethyl cellulose per liter of water while in contact with a receiving element containing copoly(styrene-co-N,N,N-tri-n-hexyl-N-vinylbenzylammonium chloride) at 2.15 g./m.$^2$ and gelatin at 2.15 g./m.$^2$.

After 10 min., the photosensitive element and the receiver element were separated and the reflection densities of the transferred dyes were measured on the receiver as follows:

| Exposure | Reflection of the Dye Density | | |
|---|---|---|---|
| | Red | Green | Blue |
| none | 1.86 | 1.54 | 1.64 |
| white | 0.28 | 0.41 | 0.36 |
| yellow | 0.30 | 0.52 | 1.24 |
| magenta | 0.44 | 1.18 | 0.60 |
| cyan | 1.78 | 0.75 | 0.56 |
| red | 0.41 | 1.30 | 1.52 |
| green | 1.78 | 0.86 | 1.39 |
| blue | 1.93 | 1.50 | 0.82 |

EXAMPLE 20

A photographic element was prepared by coating a polyethylene terephthalate film support with a layer containing gelatin at 2.16 g./m.$^2$, a negative-working silver bromide emulsion at 1.08 Ag/m.$^2$, an aromatic nitro compound at 3.78×10$^{-4}$ moles/m.$^2$ and a hydrolyzable electron donor at 7.56×10$^{-4}$ moles/m.$^2$. The aromatic nitro compound and the electron donor were dissolved in an equal weight of diethyl lauramide and dispersed together in gelatin before coating. A suitably hardened overcoat layer containing gelatin at 0.86 g./m.$^2$ was then applied.

Samples of the element were imagewise-exposed through a graduated density test object and processed by rupturing pods containing a portion of viscous processing compositions containing 51 g. of potassium hydroxide, 20 g. of potassium bromide, 3.0 g. of 4-hydroxymethyl-4-methyl-1-phenyl-3-pyrazolidone, 51 g. of carboxymethyl cellulose and 1.0 g. of 5-methylbenzotriazole/liter of water while in contact with samples of a receiver element containing the dye mordant poly(-divinylbenezene—co-styrene—co-N-benzyl-N,N-dimethyl-N-vinylbenzylammonium chloride).

After 10 min., the photosensitive elements and the receiver were separated, and well-defined, positive dye images were observed in each receiver element. The minimum and maximum densities to the appropriate light sources of each dye image were measured and are recorded in the following table:

| Element | Compound No. | Electron Donor No. | 5-Methyl-benzotri-azole (g./l.) | Dmax | Dmin |
|---|---|---|---|---|---|
| A | XIII | ED-5 | 1 | 1.65 | 0.16 |
| B | XIV | ED-5 | 1 | 2.26 | 0.41 |

EXAMPLE 21

Three-color integral-negative receiver color transfer element and process

A photographic integral-imaging-receiver transfer element was prepared by coating a transparent polyethylene terephthalate film support with the following layers in order from the support:

Layer 1—a receiving layer containing gelatin at 2.16 g./m.² and poly(styrene-co-N,N,N-tri-n-hexyl-N-vinylbenzylammonium chloride) at 2.16 g./m.²;

Layer 2—a white reflecting layer containing gelatin at 3.89 g./m.² and titanium dioxide at 21.6 g./m.²;

Layer 3—an opacifying layer containing gelatin at 2.7 g./m.² and carbon at 1.62 g./m.²;

Layer 4—a red-sensitive, cyan dye-providing layer containing a red-sensitized, negative-working silver bromoiodide emulsion at 1.08 g. Ag/m.², Compound I at 0.42 g./m.², Electron Donor No. ED-1 at 0.64 g./m.², 2,4-di-n-amylphenol at 1.06 g./m.² and gelatin at 2.16 g./m.²;

Layer 5—an interlayer containing gelatin at 1.62 g./m.², 2,5-di-sec-dodecylhydroquinone at 0.22 g./m.², diethyl lauramide at 0.16 g./m.² and a magenta filter dye;

Layer 6—a green-sensitive, magenta dye-providing layer containing a green-sensitized, negative-working silver bromoiodide emulsion at 1.62 g. Ag/m.², Compound XV at 0.67 g./m.², Electron Donor No. ED-1 at 1.22 g./m.², 2,4-di-n-amylphenol at 1.89 g./m.² and gelatin at 3.24 g./m.²;

Layer 7—an interlayer containing gelatin at 2.16 g./m.², 2,5-di-sec-dodecylhydroquinone at 0.22 g./m.² and a yellow filter dye;

Layer 8—a blue-sensitive, yellow dye-providing layer containing a blue-sensitized, negative-working silver bromoiodide emulsion at 1.62 g. Ag/m.², Compound VI at 0.58 g./m.², Electron Donor No. ED-1 at 1.32 g./m.², 2,4-di-n-amylphenol at 1.89 g./m.² and gelatin at 3.24 g./m.²; and Layer 9—a hardened overcoat layer containing gelatin at 0.86 g./m.².

A sample of the above-prepared photographic element was selectively exposed through a multicolor graduated-density test object comprising white, red, green, blue, cyan, magenta and yellow filtered light sources, each focused on a separate portion of the element.

The exposed sample was processed at 24° C. by laminating to a processing cover sheet and rupturing a pod containing a portion of a viscous processing composition comprising 51 g. of potassium hydroxide, 20 g. of potassium bromide, 3.0 g. of 4-hydroxymethyl-4-methyl-1-phenyl-3-pyrazolidone, 2.0 g. of 5-methylbenzotriazole, 51 g. of carboxymethyl cellulose and 1.0 liter of water.

The cover sheet is of the type disclosed by Hannie and Ducharm, U.S. Ser. No. 676,947 filed Apr. 14, 1976, which consists of a transparent polyethylene terephthalate film support having coated thereon:

(1) a layer of poly(butylacrylate-co-acrylic acid)
(2) a timing layer containing a mixture of cellulose acetate and poly(styrene-co-maleic anhydride); and
(3) a second timing layer containing a latex dispersion of poly(acrylonitrile-co-vinylidene chloride-co-acrylic acid).

In addition, an opaque backing was applied to the opposite side of the cover sheet support to allow processing in ambient light.

After 15 min., the densities to red, green and blue light were measured and are recorded in the following table.

| Exposure | Reflection Density | | |
|---|---|---|---|
| | Red | Green | Blue |
| cyan | 1.30 | 0.50 | 0.45 |
| magenta | 0.34 | 1.40 | 0.65 |
| yellow | 0.18 | 0.46 | 1.75 |
| white | 0.18 | 0.35 | 0.48 |
| red | 0.36 | 1.62 | 1.95 |
| green | 1.72 | 0.60 | 1.85 |
| blue | 2.00 | 1.85 | 0.85 |
| none | 1.80 | 1.76 | 1.93 |

In the above example, good results are also obtained when a transparent cover sheet is used along with a processing composition containing sufficient carbon in the processing composition to preclude adverse exposure to roomlight through the layer of processing composition.

Although the invention has been described in considerable detail with particular reference to certain preferred embodiments thereof, variations and modifications can be effected within the spirit and scope of the invention.

We claim:

1. A compound having the formula:

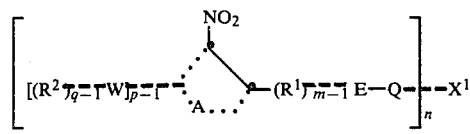

where A represents a group containing the atoms necessary to form a 5- or 6-membered aromatic ring with the remainder of said formula; W is an electron withdrawing group having a positive Hammett sigma value; $R^2$ is a hydrogen atom, an alkyl group containing from 1–30 carbon atoms, or an aryl group containing from 6–30 carbon atoms; $R^1$ is a bivalent organic group containing from 1–3 atoms in the bivalent linkage; m and q are positive integers of 1 or 2; p is a positive integer of 1 or greater, and p is 1 only when A contains an aromatic 'onium group, and when p is 2, the substituent $[(R^2)_q$-TW] is ortho or para to the nitro group on said formula; E and Q provide an electrophilic cleavage group where E is an electrophilic center, and Q is a bivalent group providing a monoatom linkage between E and $X^1$ wherein said bivalent group is an oxygen atom, a sulfur atom, a selenium atom or a nitrogen atom providing an amino group; n is an integer of 1–3; and $X^1$, together with Q is either an image dye-providing material or a photographic reagent.

2. A compound according to claim 1 wherein Q—$X^1$ is a dye.

3. A compound according to claim 1 wherein E is a carbonyl group.

4. A compound according to claim 1 wherein p is an integer of 2-5 and A is a group which provides a carbocyclic aromatic group.

5. A compound according to claim 1 wherein p is 3 and one of said groups represented by W is a bivalent sulfonyl group and one of said groups represented by W is a monovalent electron-withdrawing group.

6. A compound having the formula:

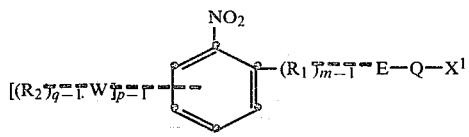

wherein q and m are positive integers of 1 or 2 and p is a positive integer of 3-5; W is an electron-withdrawing group having a positive Hammett sigma value; $R^2$ is an alkyl group containing from 1-20 carbon atoms or an aryl group containing from 6-40 carbon atoms; $R^1$ is a bivalent organic group containing from 1-3 atoms in the bivalent linkage; E and Q provide an electrophilic cleavage group where E is an electrophilic center which is a carbonyl group or a sulfonyl group, and Q is a bivalent group providing a monoatom linkage between E and $X^1$ wherein said atom is an oxygen atom, a sulfur atom, a selenium atom or a nitrogen atom which forms an amino group; and $X^1$ is a dye-providing moiety or a photographic reagent.

7. A compound according to claim 6 wherein W is a sulfonyl group, p is an integer of 3, and q is an integer of 2.

8. A compond having the formula:

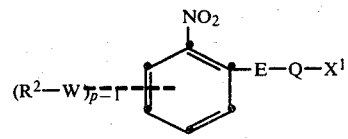

wherein p is a positive integer of 1-5; W is an electron-withdrawing group having a positive Hammett sigma value; $R^2$ is an alkyl group containing from 1-20 carbon atoms or an aryl group containing from 6-40 carbon atoms; E and Q provide an electrophilic cleavage group where E is an electrophilic center which is a carbonyl group or a sulfonyl group, and Q is a bivalent group providing a monoatom linkage between E and $X^1$ wherein said atom is an oxygen atom, a sulfur atom, a selenium atom or a nitrogen atom providing an amino group; and $X^1$ is a dye-providing moiety or a photographic reagent.

9. A compound according to claim 8 wherein Q—$X^1$ is an image dye-providing moiety.

10. A compound according to claim 8 wherein Q—$X^1$ is an azo dye.

11. A compound having the formula:

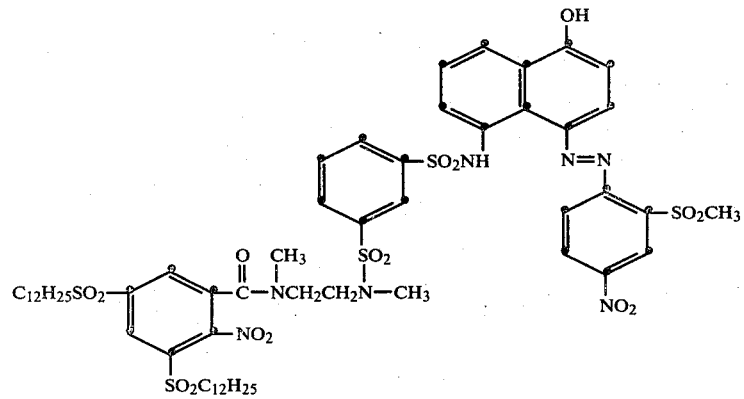

12. A compund having the formula:

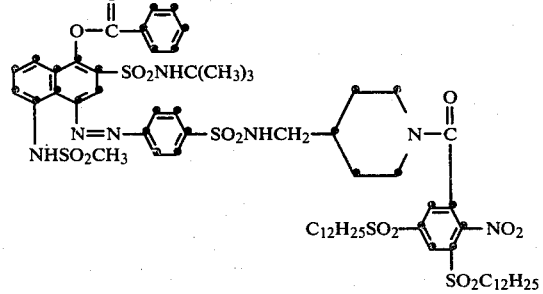

* * * * *